United States Patent [19]
Pullman et al.

[11] Patent Number: 5,294,549
[45] Date of Patent: Mar. 15, 1994

[54] METHOD FOR REPRODUCING CONIFERS BY SOMATIC EMBRYOGENESIS USING MIXED GROWTH HORMONES FOR EMBRYO CULTURE

[75] Inventors: Gerald S. Pullman, Renton; Pramod K. Gupta, Federal Way, both of Wash.

[73] Assignee: Weyerhaeuser Company, Tacoma, Wash.

[21] Appl. No.: 814,976

[22] Filed: Dec. 23, 1991

Related U.S. Application Data

[63] Continuation-in-part of Ser. No. 705,681, May 24, 1991, Pat. No. 5,236,841, which is a continuation-in-part of Ser. No. 499,151, Mar. 26, 1990, Pat. No. 5,036,007, which is a continuation-in-part of Ser. No. 321,035, Mar. 9, 1989, Pat. No. 4,957,866, and Ser. No. 426,331, Oct. 23, 1989, Pat. No. 5,034,326.

[51] Int. Cl.$^5$ .................... A01H 4/00; A01H 1/00
[52] U.S. Cl. .................... 435/240.45; 435/240.48; 435/240.49; 435/240.54; 435/240.46; 47/58 MS; 800/200; 800/DIG. 49
[58] Field of Search .................... 800/200; 435/240.4, 435/240.45, 240.47, 240.49, 172.1; 47/58.05, DIG. 49

[56] References Cited

U.S. PATENT DOCUMENTS

| | | | |
|---|---|---|---|
| 4,957,866 | 9/1990 | Gupta et al. | 435/240.4 |
| 5,034,326 | 7/1991 | Pullman et al. | 435/240.4 |
| 5,036,007 | 7/1991 | Gupta et al. | 435/240.45 |

FOREIGN PATENT DOCUMENTS 293598 12/1988 European Pat. Off. .

OTHER PUBLICATIONS

Durzon et al. (1987) Plant Science vol. 52 pp. 229–235.
Hakman et al. (1985) J. Plant Physiology vol. 121 pp. 149–158.
Gupta et al. (1987) Biotechnology vol. 5, Feb. pp. 147–151.
Ammirato, Philip V. 1977 Hormonal control of somatic embryo development from cultured cells of caraway: interactions of abscisic acid, zeatin, and gibberellic acid. *Plant Physiology* 59: 579–586.
1983 The regulation of somatic embryo development in plant cell cultures: suspension culture techniques and hormone requirements. *Bio/Technology* 1(3): 68–74.
Chalupa, V. 1990a Somatic embryogenesis and plant regeneration in *Quercus petrae* (Matt.) Liebl., *Tilia platyphyllos* Scop. and *Aesculus hippocastaum* L. *Lesnictvi* (Prague) 36: 599–604.

(List continued on next page.)

Primary Examiner—Gary Benzion

[57] ABSTRACT

The invention is a method for reproducing coniferous trees by somatic embryogenesis using plant tissue culture techniques in a multistage culturing process. A suitable explant, typically the fertilized embryo excised from an immature seed, is first cultured on a medium that induces multiple early stage proembryos. These are multiplied in a second culture having reduced growth hormones. The early stage embryos may then be placed in or on a late stage proembryo development culture in order to develop very robust late stage proembryos having at least 100 cells. Culturing from this point continues in a cotyledonary embryo development medium containing an active gibberellin (GA) in an amount up to about 50 mg/L. Preferably exogenous abscisic acid (ABA) is also present in a similar amount. Concentration of GA and ABA may be reduced over time by inclusion of an adsorbent such as activated charcoal or by stepwise subcultures in which the later cultures have reduced hormone concentrations. After several weeks somatic embryos having the appearance of zygotic embryos will have formed. These may be germinated before or after storage and transplanted to soil for further growth. In addition to its use in the cotyledonary embryo development stage, GA may also be advantageously included in any of the maintenance cultures following embryo initiation. The use of GA results in larger and more robust somatic embryos and ultimately in greater germination success.

20 Claims, 2 Drawing Sheets

OTHER PUBLICATIONS

1990b Plant regeneration by somatic embryogenesis from cultured immature embryos of oak (*Quercus robur* L.) and linden (*Tilia cordata* Mill. *Plant Cell reports* 9:398–401.

Cruz, Gil S., Jorge M. Canhoto, and Maria A. V. Abreu 1990 Somatic embryogenesis and plant regeneration from zygotic embryos of *Feijoa sellowiana* Berg. *Plant Science* 66: 263–270.

Eapen, S., V. Abraham, M. Gerdemann, and O. Schieder 1989 Direct somatic embryogenesis, plant regeneration and evaluation of plants obtained from mesophyll protoplasts of *Brassica juncea. Annals of Botany* 63: 369–372.

Eapen, Susan, and Leela George 1990 Ontogeny of somatic embryos of *Vigna aconitifolia, Vigna mungo* and *Vigna radiata. Annals of Botany* 66: 219–226.

Evans, M. L. 1984 Functions of hormones at the cellular level of organization. In *Hormonal Regulation of Development II*, Tom K. Scott Ed., pp. 23–79, Springer-Verlag, New York.

Ferriera, Alfredo Gui, Ching Yeh-Hu, and E. R. Santarem 1990 Somatic embrogenesis of soybean *Glycine max* (1.) Merrill, Brazilian cultivars Ivorá and IAS-5. *Phyton* (Buenos Aires) 51(2): 139–144.

Garcia-Maya, M., J. M. Chapman, and M. Black 1990 Regulation of α-amylase formation and gene expression in the developing wheat embryo: role of abscisic acid, the osmotic environment and gibber-ellin. *Planta* 181: 296–303.

Ghosh, Biswajit and Sumitra Sen 1991 Plant regeneration through somatic embryogenesis from spear callus culture of *Asparagus cooperi* Baker. *Plant Cell Reports* 9: 667–670.

Gmitter, F. G. Jr., X. B. Ling, and X. X. Deng 1990 Induction of triploid citrus plants from endosperm calli in vitro. *Theoretical and Applied Genetics* 80: 785–790.

Gupta, Pramod K. and Don J. Durjan 1986 Plantlet regeneration via somatic embryogenesis from subcultured callus of mature embryos of *Piceaabies* (Norway spruce). *In Vitro Cellular & Developmental Biology* 22: 685–688.

Hakman, Inger and Sara von Arnold 1988 Physiological Plantarium 72: 579–587.

Kochba, J., P. Spiegel-Roy, H. Neumann, and S. Saad. 1978 Stimulation of embryogenesis in citrus ovular callus by abscisic acid, ethepon, 2-chloroethyltrimethyl ammonium chloride, and Alar and its suppression by gibberellic acid. *Z. Pflanzenphysiol. Bd.* 89: S. 427–432.

Lakshmi Sita, G. 1985 Sandalwood (*Santalum album*). In *Biotechnology in Agriculture and Forestry 1: Trees I*, Y. P. S. Bajaj, ed. Springer-Verlag, New York.

Manrique, S. L. and W. Roca 1987 Effect of the photoperiod and the culture medium on somatic embryogenesis and a histological analysis of the process in the cassava *Manihot esculenta* Crantz. *Acta Agronomica* (Palmira) 37(2): 7–18.

Nolan, Randall C. and Tuan-Hua David Ho 1988 Hormonal regulation of α-amylase expression in barley aleurone layers: the effects of gibberellic acid removal and abscisic acid and phaseic acid treatments. *Plant Physiology* 88: 588–593.

Noriega, Clemencia and Maro R. Söndahl 1991 Somatic embryogenesis in hybrid tea roses. *Bio/Technology* 9: 991–993.

Rajasekaran, K., M. B. Hein, and I. K. Vasil 1987 Endogenous abscisic acid and IAAA and somatic embryogenesis in cultured leaf explants of *Pennisetum purpureum* Schum.: effects in vivo and in vitro of glyphosphate fluridone, and paclobutrazol. *Plant Physiology* (Bethesda) 84: 47–51.

Rangaswamy, N. S. 1986 Somatic embryogenesis in angiosperm cell tissue and organ cultures. *Proceedings Indian Academy of Sciences (Plant Sciences)* 96(4): 247–271.

Tisserat, Brent and Toshio Murashige 1977 Probable identity of substances in citrus that repress asexual embryogenesis. *In Vitro* 13: 785–789.

Trolinder, Norma L., and J. R. Goodin 1988 Somatic enbryogenesis in cotton (Gossypium). II: requirements for embryo development and plant regeneration. *Plant Cell, Tissue and Organ Culture* 12: 43–53.

METHOD FOR REPRODUCING CONIFERS BY SOMATIC EMBRYOGENESIS USING MIXED GROWTH HORMONES FOR EMBRYO CULTURE

This invention is a continuation-in-part of our earlier application Ser. No. 705,681, filed May 24, 1991, now U.S. Pat. No. 5,236,841, which was a continuation-in-part of application Ser. No. 499,151, filed Mar. 26, 1990, now U.S. Pat. No. 5,036,007, which was in turn a continuation-in-part of applications Ser. No. 321,035, filed Mar. 9, 1989, now U.S. Pat. No. 4,957,866 and Ser. No. 426,331, filed Oct. 23, 1989, now U.S. Pat. No. 5,034,326.

BACKGROUND OF THE INVENTION

The present invention is a method for reproducing coniferous plants by somatic embryogenesis using the techniques of plant tissue culture. More specifically, it relates to the use of particular mixtures of growth hormones in the culture media used during the various stages of somatic embryo development. The invention is especially suited for producing large clones of superior selections useful for reforestation.

Loblolly pine (*Pinus taeda* L.), its closely related southern pines, and Douglas-fir (*Pseudotsuga menziesii* (Mirb.) Franco) are probably the most important commercial species of temperate North American timber trees. Similarly, Norway spruce (*Picea abies* (L.) Karst.) is probably the most important European softwood species. Since the early 1940s, when serious private reforestation efforts began, literally billions of one and two year old nursery-grown trees have been planted on cutover or burned forest lands. For many years these seedling trees were grown using naturally produced seed from cones collected as a part time effort of individuals seeking to supplement their incomes. As early as 1957 forest geneticists began to plant seed orchards using either seed or grafted scions obtained from superior trees discovered in the forests. These trees were selected for such inheritable characteristics as rapid growth, straightness of bole, wood density, etc. Now in both the southern pine and Douglas-fir regions the bulk of the seed is produced from selected trees grown in seed orchards, some of them now second and third generation orchards.

Despite the fact that the orchards were stocked with superior trees, pollination often cannot be carefully controlled and frequently the seed trees are fertilized by wild pollen of unknown characteristics. For this reason, the characteristics of the progeny produced by sexual reproduction have not been as predictable as hoped and genetic gain could not be attained as rapidly as desired.

Beginning about 1960, techniques were developed for reproducing some species of plants by tissue culture. These were predominately angiosperms and usually ornamental house plants. The method employed use of a suitable explant or donor tissue from a desirable plant. This was placed on a series of culture media in which nutrients and growth hormones were carefully controlled from step to step. The usual progression was growth from the explant to a callus. The callus was placed on a budding medium where adventitious buds formed. These, in turn, were separated, elongated, and rooted to ultimately form plantlets. A plantlet has the nature of a seedling but is genetically identical to the explant donor plant.

Gymnosperms in general, and most forest tree species in particular, proved to be much more difficult to reproduce by tissue culture. It was not until about 1975 that Douglas-fir was successfully reproduced by organogenesis. Loblolly pine was successfully reproduced about two years later.

A brief review of some of the most important work relating to the present invention will follow. This is intended to be representative only and is not fully inclusive of all the work in the field. Literature citations in the text are given in abbreviated form. Reference should be made to the bibliography at the end of the specification for full citations of the literature noted herein.

Culture by organogenesis is tedious and expensive due to the large amount of delicate manual handling necessary. It was soon recognized that embryogenesis was potentially a much more desirable method from the standpoints of quantity of plantlets produced, cost, potential genetic gain, and much lower probability of mutations. Work on embryogenesis of forest species began in the late 1970s. U.S. Pat. No. 4,217,730 to El-Nil describes one early attempt at somatic embryogenesis of Douglas-fir. This approach was later set aside because advanced stage embryos and plantlets could not be readily obtained. However, other workers entered the field in increasing numbers and progress has been rapid even if it has not until the present time reached the commercial stage.

Our earlier U.S. Pat. Nos. 4,957,866, 5,034,326, 5,036,007, herein incorporated by reference, describe improved methods of conifer embryogenesis. These also include extensive reviews of the most closely related literature. In the methods described in all of these patents, late stage proembryos, defined as totipotent embryonic structures having at least about 100 cells, are transferred and further cultured in a cotyledonary embryo development medium containing abscisic acid (ABA) as an essential growth hormone. It appears to be highly desirable during this stage to gradually reduce the level of exogenous ABA so that little or none is ultimately present. Other growth hormones; e.g. auxins, cytokinins, and gibberellins were not used at this time. The ultimate product of this culturing step is somatic embryos resembling natural mature zygotic embryos in morphology.

It is well accepted that plant tissue culture is a highly unpredictable science. Sondahl et al., in published European Patent Application 293,598, speak directly to this point.

"Since each plant species appears to possess a unique optimal set of media requirements, the successful preparation and regeneration of a new species cannot be necessarily inferred from the successful regimens applied to unrelated plant species."

This statement can be carried even farther. Rangaswamy (1986) notes that the potential for embryogenesis is even genotype specific within any given species.

Composition of the media used to initiate embryogenesis and induce embryo maturation are critical to success, regardless of the species being propagated. In particular, the type and level of the nitrogen source in the media and the presence or absence, composition, level, and timing of availability of growth hormones have been key to success. It is also these very factors, particularly the hormones, that have proved to be so unpredictable. As one example, Ammirato (1977), conducted a study examining the effects of zeatin (a cytokinin), ABA, and gibberellic acid ($GA_3$) on the yield and morphology of caraway (*Carum carvi*) somatic embryos. These hormones were present singly and in all possible combinations in the media used for the later stages of embryo development. He concluded that a change in level or presence/absence of any one of the hormones caused a ripple effect felt throughout the system due to unpredictable interactions between the various hormones. The same problem is again discussed by Evans (1984) who notes that growth hormones which affect the same process can either act independently or may interact in some fashion.

The Ammirato (1977) paper is midrange in time between the first successful plant embryogenesis and the present. Much has been learned since then. However, this paper is useful in its clear and still valid presentation and characterization of the various growth hormones as promoters (or stimulators) and inhibitors. Evans (1984) once again expands Ammiratto's discussion. Auxins are seen by these investigators as promoting cell elongation, especially in shoot tissues, and in lower concentrations, in roots. Gibberellic acid ($GA_3$) also promotes cell elongation in shoots but is either without effect or inhibitory in root tissues. ABA and ethylene are seen as inhibitors and tend to counteract the promotive effects of auxins and GA. Cytokinins appear to be more difficult to characterize. They generally tend to inhibit auxin induced cell elongation in stem and root tissues but act as promoters of leaf cell expansion.

In general, as far as conifer species are concerned, it appears that at least one exogenous auxin and usually a cytokinin are necessary hormones in a medium for the initiation of embryogenesis. Exogenous ABA is normally not used at this point nor is gibberellic acid ($GA_3$) or its related gibberellins. The concentration of the growth hormones used in the initiation medium is typically then reduced or they are removed entirely as embryo development proceeds. However, auxins in particular may be beneficial at the stage of cotyledonary embryo development.

In most cases gibberellic acid appears to suppress embryogenesis; e.g., Kochba et al. (1978), Tisserat et al. (1977), Rajasekaran et al. (1987), Rangaswamy (1986). However, there are certainly exceptions. Chalupa (1990a, 1990b) refers to induction of embryogenesis in two Quercus species on a medium containing the cytokinin $N^6$-benzylaminopurine and gibberellic acid. Gmitter et al. (1990) appear to require gibberellic acid in their initiation medium for selected triploid hybrid citrus plants. Lakshmi Sita (1985) summarizes her earlier work and that of others in promoting embryogenesis of sandalwood (Santalum sp.). Gibberellic Acid was found to be useful in inducing embryogenesis using shoot explants in either solid or liquid suspension cultures. Despite her success, which included successful production of converted plants, she again points to the lack of predictability of embryogenesis.

"Despite progress, our knowledge of embryogenesis is still fragmentary. At present we cannot yet define the conditions necessary for embryogenesis . . . "

Gibberellic acid has more frequently been used to promote late stage somatic embryo development and germination; e.g., Cruz et al. (1990), Eapen et al. (1990), Ghosh et al. (1991), Manrique et al. (1987), Trolinder et al. (1988). Nolan et al. (1988) and Garcia-Maya et al. (1990) note that gibberellins are involved in the synthesis of $\alpha$-amylase. This enzyme is necessary for conversion of starches into sugars during germination.

Much less frequently various gibberellins have been used in combination with ABA at the late stage of embryo development and for stimulating germination; e.g., Eapen et al. (1989), Ferreira et al. (1990), Sondahl et al. (1988). Noriega et al. (1991) describe the first successful regeneration of hybrid tea rose by embryogenesis. Among the various media employed is an embryo maturation medium containing low concentrations of $GA_3$ and ABA. Ammirato (1977), working with caraway (*Carum carvi* L.), reported that the beneficial effects of ABA on embryo maturation could be enhanced by gibberellic acid ($GA_3$). However, in an extension of this work investigating the effect of mode of agitation, he noted that "the addition of $GA_3$, alone or with ABA, had little effect on these cultures" (Ammirato (1983)). All of the reported work with this particular hormone combination has been exclusively with various angiosperm species.

The present inventors are aware of only one reported instance in which gibberellic acid has been examined in conifer somatic embryogenesis. Hakman and von Arnold (1985) tried adding ABA, IAA (indoleacetic acid), $GA_3$, $GA_{4/7}$, and activated charcoal singly to media used for further development of *Picea abies* (Norway spruce) proembryos. All of these were found to be ineffective and only a cytokinin-containing medium was useful under the conditions they employed.

Techniques to promote embryogenesis of numerous conifer genera are now well established. Research emphasis is now shifting to development of ways to scale up laboratory knowledge and techniques so that the process may become field operational on large scale. Yet many problems of a relatively fundamental nature still remain to be solved. One of these is improving somatic embryo quality and vigor. This is necessary so that germination to hardy plantlets and ultimate conversion to growing trees can be achieved at much higher percentages than has heretofore been possible. The present invention is directed to this end.

SUMMARY OF THE INVENTION

The present invention is directed to the use of various gibberellins in the media at the different stages of conifer embryogenesis. It is particularly directed to new combinations of growth hormones during the cotyledonary embryo development stage of conifer somatic embryogenesis. We have also found that the inclusion of gibberellins in the medium used for proembryo maintenance results in more robust proembryos. Addition of gibberellins at this stage enables further development of many genotypes that were previously found difficult to culture. We have also found that a combination of abscisic acid and various gibberellins is advantageous in promoting the growth of more robust somatic embryos of coniferous species when used at the cotyledonary embryo stage of development. These embryos closely resemble natural mature zygotic embryos in external and internal morphology. Conversion success of embryos produced using the new hormone regimen has been significantly improved over those made using previous culturing techniques.

The present method is especially suitable for reproducing woody gymnosperms of the order Coniferales. It is particularly well suited for generating large clones of superior forest trees for reforestation, including species within the families Pinaceae, Cupressaceae, and Taxodiaceae. Most or all species within the genera Abies, Pinus, Picea, Tsuga, Pseudotsuga, Thuja, Juniperis, Larix, Taxus and Sequoia are believed to be amenable to multiplication by the present method.

The method is particularly advantageous tin that it enables more robust somatic embryos to be produced. This results in higher numbers of embryos that can be successfully converted into plants growing in soil. Cost per plant can be significantly reduced over prior known tissue culture methods. In addition, use of the method generates proembryos that can be retained for extended periods of time in cryogenic storage. Alternatively, cotyledonary embryos are produced that can be held in cold storage for prolonged periods without the need to transfer them from the development medium.

A number of terms are known to have differing meanings when used in the literature. The following definitions are believed to be the ones most generally used in the field of botany and are consistent with the usage of the terms in the present specification.

"Auxins" are plant growth hormones that promote cell division and growth.

"Cytokinins" are plant growth hormones that affect the organization of dividing cells.

"Callus" is generally considered to be a growth of unorganized and either unconnected or loosely connected plant cells generally produced from culturing an explant.

"Embryogenic callus" is a translucent white mucilaginous mass that contains early stage proembryos attached to suspensors. This is also referred to as an "embryonal-suspensor mass" or "ESM" by some investigators.

A "proembryo" is a cell or group of cells having the potential to become a plant but lacking defined meristematic organ primordia.

Figures 1, 2, 3, 4:
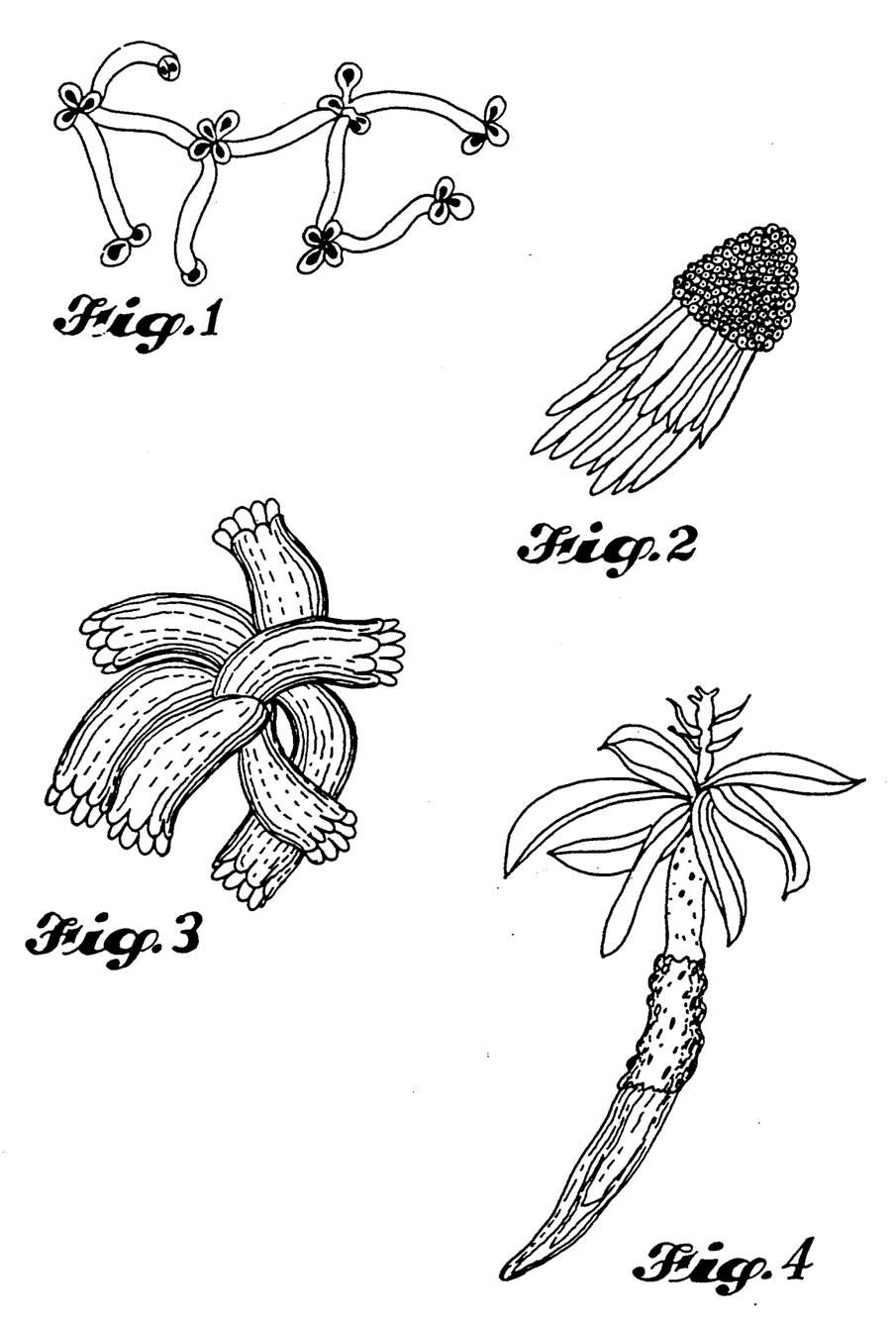
FIG. 1 shows early stage proembryos.
FIG. 2 shows late stage proembryos.
FIG. 3 depicts cotyledonary stage embryos.
FIG. 4 shows a plantlet ready for transfer to soil.

An "early stage proembryo" is a mass generally of 1-10 cells with dense cytoplasm and large nuclei that have the potential of forming a plant. The early stage proembryo is normally found as a head associated at the end of a long thin-walled suspensor cell (FIG. 1).

A "late stage proembryo" is a proembryo with a smooth embryonal head of at least about 100 cells associated with multiple suspensor cells. The late stage proembryo is a very robust advanced proembryo (FIG. 2). Many investigators refer to these as "globular embryos".

Figure 5:
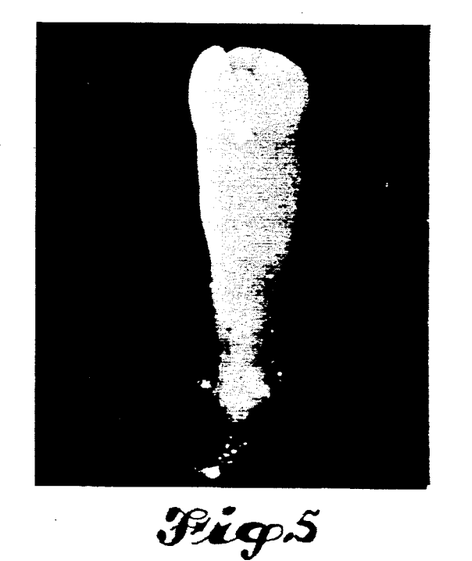
FIG. 5 is a photomicrograph of a high quality Douglas-fir cotyledonary embryo.

A "cotyledonary embryo", sometimes simply referred to as an "embryo", has a well defined elongated bipolar structure with latent meristematic centers having cotyledonary primordia at one end and a potential radicle at the opposite end. The cotyledonary structure frequently appears as a small "crown" at one end of the embryo (FIGS. 3 and 5). A cotyledonary somatic embryo is analogous to a developed zygotic embryo.

An "explant" is a piece of tissue taken from a donor plant for culturing.

"Gibberellins" are plant growth hormones which serve to promote cell elongation. They are closely related members in a chemical genus of over 70 known compounds. Gibberellins $GA_3$, $GA_4$, $GA_7$, and mixtures of the latter two designated $GA_{4/7}$ are the most commonly used due to their relatively greater availability and much lower cost.

"Gibberellic acid" is an unspecified mixture of gibberellins. When referred to in the more recent literature it usually designates a composition with at least 70% $GA_3$. In the present application the term "GA" or "GAs" without a specific numeric designation is used in a generic sense to represent an active gibberellin.

An "active gibberellin" is one that is biologically active in the particular plant species being cultured.

A "meristem" or "meristematic center" is a group of tissue forming cells capable of further development into plant organs; e.g., shoots and roots.

An "osmoticant" or "osmoticum" is a chemical material used for controlling the osmotic potential of a solution. In the present context the solution would be a culture medium.

A "plantlet" is a plant asexually reproduced by tissue culture (FIG. 4).

A "converted embryo" is an embryo that has germinated and been established as a plant growing in soil.

"Somatic embryogenesis" is the process using tissue culture techniques for generating multiple embryos from an explant. The embryos generated from a given tissue source are presumed to be genetically identical.

The present method as a whole comprises a multistage culturing process. A suitable explant is first placed on an induction or initiation culture medium. This will usually contain relatively high quantities of growth hormones including at least one auxin and frequently one or more cytokinins. However, growth hormones at this initial stage are not always necessary or desirable for induction of early stage proembryos. A number of sources of explants may ultimately prove to be satisfactory for culturing. These include, but are not limited to, tissue from cotyledons, hypocotyls, epicotyls, buds, meristematic centers for buds or roots, and seed embryos. Zygotic embryos removed from seeds are presently preferred. In particular, for species which in the past have proved to be very difficult or impossible to propagate by somatic embryogenesis, the embryos from immature seeds may be preferred. In the case of Douglas-fir, an embryo selected between the time that an apical dome begins to form but before the first appearance of cotyledon primordia appears to be optimum.

The first stage or induction medium will normally be one of those well known from past work which contain a balanced concentration of inorganic salts and organic nutrient materials, with plant growth hormones included as noted above. Auxins are normally present in concentrations which may initially be as high as about 600 $\mu M/L$, more typically not exceeding about 500 $\mu M/L$. Cytokinins, if present, may initially be as high as 500 $\mu M/L$. The plant growth hormones may include at least one auxin and one cytokinin in a combined initial concentration not exceeding about 1100 $\mu M/L$, more typically not exceeding about 900 $\mu M/L$. The particular auxins and cytokinins used and their exact concentrations, or whether they are used at all, will depend somewhat on the species being cultured and even on the particular genotype within that species. This is something that cannot be easily predicted but can be readily determined experimentally. These very high levels of growth hormones assume the presence in the medium of an adsorbent material, such as activated charcoal. Where charcoal is not present the levels of growth hormones would normally be much lower; e.g., a full order of magnitude, than those just noted.

Culturing during this stage may be carried out in the dark, under very low light conditions, or in full light until an embryogenic mass forms. Lighting conditions will depend in large part on the composition of the particular medium selected. In general, initiation in full dark is preferred. This embryogenic mass has been described by various other names by researchers who have reported it in the past; e.g., embryogenic callus (Hakman and von Arnold 1985) or embryonal-suspensor mass (Durzan and Gupta 1987). It has the appearance of a whitish, translucent, mucilaginous mass containing early stage proembryos which are readily apparent by low power light microscopy. In the case of Douglas-fir the presence of activated charcoal or a similar adsorbent in the initiation medium appears to be quite advantageous. It should be noted here that Douglas-fir does not experience polyembryony as do most other coniferous species. The reasons for this are not well understood but one hypothesis suggests that Douglas-fir seeds contain a high endogenous level of abscisic acid which suppresses polyembryony. Activated charcoal in the initiation medium may remove this endogenous ABA, as well as other undesirable metabolic byproducts, to allow polyembryony to occur in vitro. Because the charcoal will also gradually remove growth hormones over time the initial concentrations of these materials are necessarily higher than might otherwise be the case. The preferred induction medium for Douglas-fir will preferably contain an auxin or auxins in amounts of about 400–600 $\mu$M/L and a cytokinin or cytokinins in the amount of about 240–500 $\mu$M/L in combination with 0.05–1.0% activated charcoal.

Early stage proembryos from the first culture may be directly transferred to a late proembryo development culture medium having significantly reduced plant growth hormones and, for some species, a higher concentration of osmoticants. However, they are preferably first subcultured in a maintenance medium of similar or slightly higher osmotic potential than the induction medium for multiplication. This multiplication medium will also usually have the concentration of plant hormones significantly reduced below that of the induction medium. By "significantly reduced" is meant lowered by a factor which may typically be one whole order of magnitude. In the case of Douglas-fir it may be two full orders of magnitude below that initially present in a charcoal containing induction medium. No hormone adsorbent is usually necessary or desirable at this time. The osmotic potential of the induction and maintenance medium will most usually not exceed about 160 mM/kg.

The composition and use of the late proembryo development culture medium is important to the success of the present process. It differs from the induction medium by having a similar level of plant growth hormones to those present in the maintenance and multiplication medium. However, for many species such as *Pinus taeda* and *Pseudotsuga menziesii*, the late proembryo development media should have a concentration of osmoticants that is significantly raised above that of the induction or multiplication media. The optimum osmoticant levels at each stage will usually differ for each species and often for individual genotypes within a species. For loblolly pine the osmotic level should typically be of the magnitude of at least 200 mM/kg and preferably about 240 mM/kg or even higher. However, lower levels of about 170 mM/kg minimum will suffice for most genotypes of Douglas-fir. The key advantage of this osmotic "pulse" is that proembryo quality and/or size can be significantly improved. Some species such as *Picea abies*, which are relatively easy to reproduce, may not require this raised osmotic level, or it may only be necessary for some genotypes. In these cases late proembryo development may usually be achieved without a change in medium composition from the maintenance and multiplication medium.

It appears now that the inclusion of between 0.05 and 15 mg/L, preferably about 0.1–5 mg/L, of selected active gibberellins and/or abscisic acid in the maintenance and/or late proembryo development media is also beneficial for improvement of proembryo quality.

Incubation at this stage is usually carried out in the dark or in greatly reduced light until robust late stage proembryos have formed. These may then be transferred to an embryo development medium which usually lacks auxins and cytokinins entirely.

Many investigators refer to cotyledonary embryo development from proembryos simply as a "development" stage and that usage will be understood herein unless the word "development" is otherwise qualified.

Douglas-fir generally requires an intermediate step between the late proembryo growth stage and the final cotyledonary embryo development stage which is not necessary for other species. The proembryos tend to form in tight clumps or clusters which must first be singulated before going to the development stage. This singulation is carried out in a series of liquid shake cultures which lack auxins and cytokinins but have exogenous abscisic acid as a necessary new hormone. The level of osmotic potential is also reduced from that of the late stage proembryo development medium. ABA will initially usually be within the range of 5–15 mg/L (20–60 $\mu$M/L) with osmotic potential levels in the range of 130–160 mM/kg. Typically the singulation process will encompass two or three transfers at weekly intervals following the initial singulation treatment. A preferred procedure uses an initial treatment with ABA at a 10 mg/L level followed by two treatments at weekly intervals with ABA at a 5 mg/L concentration. It now appears to be beneficial to include from 0.05–15 mg/L, preferably about 0.1–10 mg/L, of an active gibberellin in the singulation medium.

Further development and enlargement of the proembryos will occur during the singulation stage for Douglas-fir.

The singulated late stage proembryos can then be transferred to a solid or pad-on-liquid cotyledonary embryo development medium. If the embryos are not singulated they will develop into a tight clump of cotyledonary embryos which cannot be readily separated and are difficult to use for further germination.

Significantly, species other than Douglas-fir can be advantageously cultured by beginning early cotyledonary embryo development in a series of media similar to those used for Douglas-fir singulation.

The singulation stages are preferably carried out in Douglas-fir culture in liquid media under gently agitated conditions. Other species may produce better results if the early development cultures are made on solid medium or on pad systems using liquid medium. However, for all species it is most desirable for a final development stage or stages to be carried out on either solid medium or with liquid medium using a pad system. For reasons not perfectly understood, far more vigorous embryos are normally obtained when they are exposed to air in the final development stages.

Especially when Douglas-fir is being cultured, but also with some genotypes of loblolly pine and other species, the osmotic potential of the later stage cotyledonary development medium should be sharply raised above that of any of the preceding media. Initially levels may be in the 300–350 mM/kg range but these should be increased to levels of at least about 400 mM/kg as development proceeds. If development is started at levels around 300–350 mM/kg, the osmotic level may be increased during development by a complete medium change, a partial change in which some old medium is replaced, or by adding an appropriate form, such as a solution, of osmoticants to the medium without replacement of any of the original medium. Any of these changes may be considered a transfer to a "new" medium. With Douglas-fir, it is preferred that the osmotic levels at the end of the development period should be at least about 450 mM/kg although with some genotypes lower levels are acceptable. With some Douglas-fir genotypes final osmotic levels as high as 600 mM/kg have given superior results. These higher levels tend to prevent deterioration and callusing of the embryos.

Osmotic potential in the later stages of cotyledonary development is best controlled by a combination of osmoticants. One of these should be a readily metabolized carbohydrate energy source, preferably a sugar such as sucrose, glucose, fructose, maltose, or galactose. Sucrose is a preferred ingredient and may be present in amounts in the range of 2–6%. The other is a poorly metabolized osmoticant of which sorbitol, lactose, or a polyalkylene glycol would be examples. In a solid development medium, a combination of sorbitol, lactose and polyethylene glycol has proved very effective. Polyethylene glycol (PEG) alone, in concentrations of about 15–30% of the medium, has worked very well in liquid development media. The molecular weight of the PEG is not critical and may fall in the range of several hundred to several thousand. While the salts and organic components of the medium make a small contribution to the osmolality, the osmotic potential is primarily controlled by the energy-providing sugar and the other osmoticants. It is within the scope of the invention to use one combination of osmoticants at the beginning of development and transfer to a medium having a different combination at some point during the development stage.

In some cases where transfers to fresh media are made during the cotyledonary embryo development stage, especially when culturing Douglas-fir, at least the final and most preferably the penultimate media should have osmotic potentials of at least about 350 mM/kg, preferably about 400 mM/kg or higher.

For virtually all coniferous species a supply of exogenous abscisic acid is a useful hormone and media component in the development from proembryos to cotyledonary embryos. As described in our earlier U.S. Pat. Nos. 5,034,326 and 5,036,007, this was always used in combination with an adsorbent, such as activated charcoal. The adsorbent was present in a sufficient amount and form to slowly reduce the abscisic acid and remove metabolic waste products. It could not be present in such a high concentration as to deplete the abscisic acid in a very short time; e.g., in a matter of days. The combination of abscisic acid with the adsorbent usually required a higher initial concentration of abscisic acid than was the case if no adsorbent was present in the medium. Our pending application Ser. No. 705,681, filed May 24, 1991, describes cotyledonary embryo development by the use of stepwise media changes with progressively lower ABA contents. Activated charcoal or other adsorbents are not necessary using this procedure.

In the particular case of Douglas-fir, but with other species as well, we have found that the level of exogenous abscisic acid should be generally continuously lowered over time from the 5–15 mg/L normally found necessary at the beginning of the singulation step or cotyledonary embryo development stage to a level perhaps of about 1–2 mg/L, or even to zero, at the end of the development stage. Accurate measurements of abscisic acid present in the development stage have not yet been made due to the extreme difficulties of analyzing the medium. It is possible in some cases to produce cotyledonary embryos without exogenous ABA in the development medium. However, the embryos so produced are usually of inferior quality.

A significant discovery of the present invention is the advantage of including an active gibberellin along with abscisic acid in the development medium. The use of the gibberellins at this stage results in the development of larger and more mature cotyledonary embryos. Concentrations in the range of about 0.5–50 mg/L, preferably about 2.5–10 mg/L, have been found to be effective.

Following embryo development the embryos (FIG. 5) may be placed directly on a germination medium for conversion into plantlets. Alternatively, they may be converted into artificial seeds by any of a number of published processes.

The germination medium has no exogenous hormones, a lowered organic nitrogen content, and a reduced level of osmoticants. After a sufficient time in darkness followed by light, or a 16 hour light and 8 hour dark photoperiod, the cotyledonary embryos will have developed into plantlets. Douglas-fir does not require an initial dark period although an initial four day dark period is usually more satisfactory. A one week dark period is useful for Norway spruce. The time period for germination will be about 1–2 months. The resulting plantlets will have a well developed radicle and cotyledonary structure with a growing epicotyl and are ready for planting in soil.

The present invention is primarily concerned with the composition of the proembryo maintenance media and the cotyledonary embryo development media and method of their use. In the case of Douglas-fir, the composition of the proembryo singulation medium is also a concern. In particular the addition of at least one active gibberellin to the maintenance medium and the combination of the growth hormone abscisic acid with selected gibberellins in the maintenance and/or development media gives improved size, vigor, and maturity of somatic embryos and further reduces tendency to precocious germination.

It is an object of the present invention to produce coniferous plantlets by somatic embryogenesis.

It is another object to produce a large clone of a genetically selected forest species for reforestation using the methods of somatic embryogenesis and plant tissue culture.

It is a further object to provide a method of somatic embryogenesis that will dependably and consistently provide coniferous plantlets in large quantities.

It is yet another object to provide a method of somatic embryogenesis that can dependably and consistently reproduce large clones of selected individuals of forest species that heretofore have not been successfully reproduced by this method.

It is still a further object to provide a method whereby superior genotypes of coniferous trees can be multiplied by tissue culture in the large quantities needed for reforestation.

It is also an object to provide a method that will produce somatic embryos in large quantities with improved robust morphology for conversion into plantlets.

It is a particular object to provide a method and suitable culture media for somatic embryogenesis that produces robust somatic embryos with a high percentage of conversion to plants growing in soil.

It still another object to provide a method that generates robust somatic proembryos capable of withstanding extended periods of cryogenic preservation.

These and many other objects will become readily apparent to those skilled in the art by reading the following detailed description, taken in conjunction with the drawings.

BRIEF DESCRIPTION OF THE DRAWINGS

The figures show various stages of plant embryogenesis in which.

DETAILED DESCRIPTION OF THE PREFERRED EMBODIMENTS

The process of the present invention is not limited to any single basal culture medium or to the use of specific growth hormones other than those defined in the claims. Any of a number of well known basal media, such as that of Murashige and Skoog (1962), may be used. However, the present inventors have found the basal media described in Table 1 to give excellent results, particularly when used for culturing Douglas-fir (*Pseudotsuga menziesii*). The basal media are modified for each of the various culturing stages as shown in Table 2. Similar media particularly preferred for Norway spruce (*Picea abies*) are given in Tables 7 and 8.

Gibberellins are diterpenoid acids, all which have the same basic entgibberellane ring structure. As Sponsel (1987) describes them, there are two basic types, one having 20 carbon atoms and the other having only 19, one carbon atom having been lost by metabolism. There are 72 known gibberellins, only a small portion of which have biological activity. It is not uncommon to find as many as 20 different gibberellins in given species of vascular plants. Only a few of the gibberellins are readily available commercially. These are most usually prepared by isolation from the fungus *Gibberella fujikuroi* in which they occur in some quantity as metabolites. Of the known gibberellins, 25 have been found in Gibberella. Gibberellic acid (GA$_3$) is the end product of gibberellin metabolism in *G. fujikuroi*.

DOUGLAS FIR CULTURE

As noted in the background discussion of our earlier U.S. Pat. No. 5,036,007, the embryogeny of Douglas-fir is quite different from trees such as the spruces or pines. One of these differences is seen when early stage proembryos are placed in or on a late stage proembryo development medium. Instead of single late stage embryos, Douglas-fir develops tight clumps of these embryos. Upon further development into cotyledonary embryos, these clumps remain united and the resulting product is difficult to work with for further conversion. This phenomenon had apparently been recognized earlier by Durzan and Gupta (1987) who, while they did not discuss it specifically, transferred their embryonal-suspensor masses to a liquid shake culture containing 0.5 $\mu$M abscisic acid. They note that under the influence of ABA, individual bipolar embryos were produced which were then transferred to a development medium without ABA. The present method utilizes a series of liquid shake cultures with reduced osmotic level and added abscisic acid between late proembryo development and cotyledonary embryo development stages to achieve the necessary singulation. Osmotic level is again raised to levels generally above about 450 mM/kg during the final cotyledonary embryo development stage or stages.

A basal culture medium has been developed by the present inventors specifically to give more successful initiation and multiplication of Douglas-fir. Preferred media compositions are given in the following tables. A number of ingredients may be varied in quantity, such as those that affect the level and balance between organic and inorganic nitrogen, depending on the response of individual genotypes. This response cannot be readily predicted and media optimization must largely be achieved by a combination of intuition and trial and error.

A number of abbreviations are used in the following text. These are in common use in the field of tissue culture.

BAP—N$^6$-benzylaminopurine (or N$^6$-benzyladenine), a cytokinin.

KIN—kinetin (6-furfurylaminopurine), also a cytokinin 2,4-D—2,4-dichlorophenoxyacetic acid, an auxin NAA—2-naphthylacetic acid (naphthalene-2-acetic acid), also an auxin.

ABA—abscisic acid (5-(1-hydroxy-2,6,6-trimethyl-4-oxo-2-cyclohexen-1-yl)-3-methyl-2,4-pentadienoic acid), a maturation promoter.

GA or GAs—a generic term referring to one or more of the more than 70 closely related compounds formerly known as gibberellic acid, Gibberellins promote cell growth and elongation.

GA$_n$; e.g., GA$_3$—refers to a specific gibberellin.

TABLE 1

| *Pseudotsuga Menziesii* Basic Culture Media | | |
|---|---|---|
| | Concentration, mg/L | |
| Constituent | WTC[1] | BMG[2] |
| BASAL SALTS | | |
| NH$_4$NO$_3$ | — | 206.3 |
| KNO$_3$ | varies[1] | 1170.0 |
| CaCl$_2$.6H$_2$O | 200.0 | 220.0 |
| Ca(NO$_3$)$_2$.2H$_2$O | varies[1] | — |
| KH$_2$PO$_4$ | 340.0 | 85.0 |
| MgSO$_4$.7H$_2$O | 400.0 | 185.0 |
| MnSO$_4$.H$_2$O | 20.8 | 8.45 |
| ZnSO$_4$.7H$_2$O | 8.0 | 4.30 |
| CuSO$_4$.5H$_2$O | 0.024 | 0.013 |
| FeSO$_4$.7H$_2$O | 27.85 | 13.93 |
| Na$_2$EDTA | 37.25 | 18.63 |
| H$_3$BO$_3$ | 5.0 | 3.10 |
| NaMoO$_4$.2H$_2$O | 0.20 | 0.125 |

TABLE 1-continued

Pseudotsuga Menziesii Basic Culture Media

| Constituent | Concentration, mg/L | |
|---|---|---|
| | WTC[1] | BM_G[2] |
| CoCl$_2$.6H$_2$O | 0.025 | 0.0125 |
| KI | 1.00 | 0.42 |
| ORGANIC ADDITIVES | | |
| myo-Inositol | varies[1] | 100.0 |
| Thiamine.HCl | 1.00 | 1.00 |
| Nicotinic acid | 0.50 | 0.50 |
| Pyridoxine.HCl | 0.50 | 0.50 |
| Glycine | 2.00 | 2.00 |
| L-Glutamine | varies | 450.0 |
| Casamino acids | 500.0 | — |
| Sucrose | varies | 20,000. |
| pH | 5.7 | 5.7 |

[1]Usage varies according to culturing stage and genotype.
[2]Modified Gupta and Durzan medium BM$_3$ (1986). Medium BM$_G$ of U.S. Pat. No. 5,034,326.

TABLE 2

| | Stage I Initiation | Stage II Maintenance 1 | Stage III Maintenance 2 | Stage IV Singulation | Stage V Development | Stage VI Germination |
|---|---|---|---|---|---|---|
| Basal Medium | WTC | WTC | WTC | WTC | WTC | BM$_G$ |
| KNO$_3$ | 1250[1] | 1250–2500 | 1250 | 1050 | 1000–2500 | 1170 |
| Ca(NO$_3$)$_2$.2H$_2$O | — | — | — | 200 | — | — |
| myo-Inositol | 1000 | 1000 | 1000–30,000 | 100 | 100 | 100 |
| L-Glutamine | 450 | 450 | 1000 | 1000 | 750–1500 | — |
| Amino acid mixture[2] | — | — | — | — | 290 | — |
| Sucrose | 15,000 | 30,000 | 30,000 | 20,000 | 20,000–60,000 | 20,000 |
| Supp. carbohydrate | — | — | — | — | 30,000–300,000 | — |
| 2,4-D | 110 | 1.1 | 1.1 | — | — | — |
| N$^6$-Benzyladenine | 45 | 0.22 | 0.22 | — | — | — |
| Kinetin | 43 | 0.22 | 0.22 | — | — | — |
| Abscisic acid | — | — | — | 5–15 | 0–50 | — |
| Gibberellins GA$_n$ | — | — | — | 0–15 | 0.5–25 | — |
| Activated charcoal | 2500 | — | — | — | 0–2500 | 2500 |
| Agar | 5000 | 5000 | — | — | — | 8000[4] |
| Gelrite | — | — | — | — | 3000[3] | — |

[1]All units are in mg/L (or ppm).
[2]L-Proline - 100, L-Asparagine - 100, L-Arginine - 50, L-Alanine - 20, L-Serine - 20.
[3]Not used for liquid media.
[4]Tissue culture agar.
The pH of all media are adjusted to 5.7.

It will be seen by reference to the media compositions that the features of the earlier inventions described in our parent applications are advantageously used with Douglas-fir. A raised osmotic level following initiation is desirable for good quality late proembryo development. This level will differ somewhat between genotypes within each species as it does between species. Similarly, the level of abscisic acid present should be gradually reduced during the signulation stage and also during the cotyledonary embryo development period, if exogenous ABA is used in that stage. This may be done either by the inclusion of activated charcoal in the medium or by a stepwise reduction effected by multiple transfers to media of successively lower ABA concentration. The exogenous ABA level is preferably gradually reduced from that present at the beginning of the singulation stage so that little or none is available at the end of the development period. Selected gibberellins may also be advantageous when added during the singulation stage in an amount of about 0.05–15 mg/L, preferably about 0.1–10 mg/L. However, they should be present in the medium used for cotyledonary embryo development in a concentration of about 0.5–50 mg/L, preferably at initial levels between about 2.5 mg/L and 25 mg/L.

The examples that follow represent the best mode known at present for culturing Douglas-fir by somatic embryogenesis. With two exceptions, these examples are principally directed to the cotyledonary embryo development stage. The steps prior to that time will first be briefly outlined in the following example.

EXAMPLE 1

A preferred explant for Douglas-fir is an immature zygotic embryo. Best results have been realized with embryos selected in the interval just prior to the development of an apical dome up to the time just before cotyledon primordia become visible. The cones are split longitudinally and seeds isolated from young ovuliferous scales. Seeds are sterilized by first being agitated in 10% Liqui-Nox laboratory cleaner (Alconox, Inc, New York, N.Y.) with a small additional amount of liquid surfactant for about 10 minutes. They are then rinsed in running tap water for 30 minutes. At this time they are transferred to a sterile hood and agitated in 20% H$_2$O$_2$ for 10 minutes. Following five rinses in sterile deionized water the seed coat is split and the female gametophyte removed. This is split on one side and the embryo teased out while still remaining attached to the gametophyte by the suspensor. An explant so prepared is placed on the Stage I solid initiation medium in a 50 mm petri dish. The explants are incubated in the dark from 4–8 weeks. Sucess in forming an embryonal-suspensor mass (ESM) containing proembryos varies from about 1–10% depending on a number of variable factors which presently are not well understood.

All stages of culture are carried out at temperatures which may vary between about 20°–25° C. Temperature is not generally critical and may, on occasion be varied so as to fall outside this range.

The embryonal-suspensor masses containing early stage proembryos are transferred to a solid Stage II maintenance and multiplication medium containing greatly reduced plant growth hormones and preferably a somewhat raised osmotic level. Again, culturing is carried out in the dark with subcultures made at no greater than about two week intervals. The clone can be maintained at this stage for long periods of time. Low concentrations of a gibberellin and/or abscisic acid are frequently beneficial at this stage of culture.

Early stage proembryos from the multiplication step are preferably then transferred to a liquid Stage III second maintenance medium Having a significantly raised osmotic level. An osmotic level of at least about 170 mM/kg will usually suffice for Douglas-fir although some genotypes may require levels as high as 240 mM/kg. Myo-inositol, which will normally be around 5000 mg/L, may need to be adjusted somewhat depending on the needs of the particular genotype in order to obtain optimum results. Culture is carried out in the dark and is periodically subcultured, usually weekly. Robust late stage proembryos having 100 or more cells will develop during this time, normally 3–4 weeks.

Following late proembryo development, the cultures are transferred to a Stage IV liquid medium for the singulation step referred to earlier. This has a reduced osmotic level and is free of auxins and cytokinins. Abscisic acid is a newly added hormone in an initial amount in the range of about 5–15 mg/L, more usually about 5–10 mg/L. Cultures are again carried out in the dark. From two to four subcultures are made on a weekly basis. The level of exogenous abscisic acid will drop somewhat during each subculture. It is generally preferred that the level of abscisic acid at the beginning of a new subculture should not be significantly higher than the level used in the previous subculture. A preferred schedule is one week on a medium containing 10 mg/L ABA, a second week on a medium containing 5 mg/L ABA, and a third week on a medium also with 5 mg/L ABA. This gradual decrease in ABA level will continue through the development period. As with the maintenance medium, a low concentration of an active gibberellin appears to be advantageous in the singulation media.

Following the singulation period the embryos are ready to complete their development to cotyledonary embryos. They are transferred to either a solid medium or supported on a liquid medium. This will normally contain exogenous ABA which may be present up to about 50 mg/L. More typically, ABA will not generally exceed about 10 mg/L and most usually will not initially exceed 5 mg/L and may be considerably lower. In some cases it is not necessary to add any exogenous ABA to the development medium since a sufficient amount will be carried over with the residual singulation or rinse medium accompanying the embryos when the transfer is made from the last singulation stage. The development medium will also contain from 0.5–50 mg/L of a selected gibberellin. This is preferably $GA_{4/7}$. $GA_3$ is also useful although it is somewhat less effective in most cases. Other active gibberellins would also be expected to be beneficial at this stage. In cases where an absorbent such as activated charcoal is not used in the development medium concentrations of GA and ABA will be significantly lower than the maximum levels just noted; e.g., by a full order of magnitude.

It has been found preferable for Douglas-fir to carry out development cultures entirely in the dark. Activated charcoal is preferably used in the development medium to effect ABA reduction over time but it is not essential. Particularly for Douglas-fir, a raised osmotic level in the development medium is very highly desirable. Osmotic levels should be above about 400 mM/kg and for some genotypes may advantageously be considerably higher. The effect of osmotic level is discussed in detail in our earlier U.S. Pat. No. 5,036,007.

EXAMPLE 2

This experiment was designed to test the effect of the gibberellin $GA_3$ on embryo development and subsequent germination. Late stage Douglas-fir proembryos were singulated in a three step liquid shake culture as outlined above in media containing respectively 10, 5, and 5 mg/L ABA and lacking any other growth hormones. The medium from the last stage was drained from the embryos and they were rinsed with a development medium lacking activated charcoal and containing 2.5 mg/L ABA, 20.0 g/L (2%) sucrose and no supplemental carbohydrate. The rinsed embryos were then transferred into a development medium having 750 mg/L glutamine, 50.0 g/L (5%) sucrose, 175 g/L (17.5%) polyethylene glycol 7000, 24.5 g/L (2.45%) lactose, and 1 g/L (0.1%) activated charcoal and without ABA. $GA_3$ levels were varied from 0–25 mg/L. The media were absorbed into a double thickness pad of polyester batting and the rinsed proembryos placed on top of the pad. Embryos from five different genotypes were used. One of the five genotypes did not form cotyledonary embryos under any of the conditions employed here.

Embryos without $GA_3$ averaged 1.8 mm in length. Those with 5 mg/l $GA_3$ had a mean length of 1.95 mm and those with 25 mg/L $GA_3$ averaged 2.1 mm in length. The differences between no hormone and the use of 5 or 25 mg/L $GA_3$ was statistically significant. The embryo shape of the gibberellin treated embryos, when observed under low power magnification, was improved over that lacking this growth hormone. By improved is meant that the embryos were more robust and more closely resembled zygotic embryos in size and overall morphology. Specifically, the hypocotyl and root cap length were increased in comparison to embryos cultured without GA in the medium.

Further tests of the above embryos showed improved germination percentages of the embryos cultured with 25 mg/L $GA_3$ when compared with those lacking this hormone.

EXAMPLE 3

In view of the improved embryo morphology noted in the previous example, additional experiments were conducted to further determine the effects of $GA_3$ used by itself and in combination with ABA. Earlier work has shown that ABA alone caused a very significant yield increase and that the embryos so cultured were of similar or somewhat smaller size compared with those grown in ABA free cultures. An additional trial was made using a $GA_{4/7}$ mixture without ABA. $GA_{4/7}$ was tried because it is known to be more active than $GA_3$ in some conifers when used for inducement of flowering. Singulation conditions were identical to those used in the previous example as was the rinse prior to transfer of the proembryos to the development medium. Four genotypes were tested. Three of the genotypes were those used in the previous example and were among those that had produced cotyledonary embryos. The other genotype was new to this trial. Except for the variables of GA and ABA, other components of the development media used in this test were identical to those used in Example 2. $GA_3$ concentration was varied using 0, 1, 2.5, 5, and 10 mg/L. Trials were also made using 10 and 20 mg/L ABA in combination with 5 mg/L $GA_3$. A single trial was made using $GA_{4/7}$ by itself at 5 mg/L. Two genotypes responded well and produced embryos under all conditions. The other two genotypes generally responded poorly under all conditions.

Figure 6A:
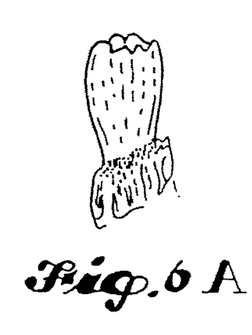
FIG. 6A is a drawing showing a conifer embryo typical of those produced prior to using the treatments of the present invention.
Figure 6B:
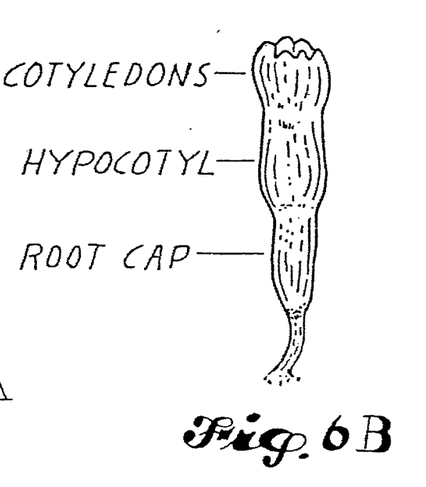
FIG. 6B is a drawing showing improvement in embryo morphology using the treatments of the present invention.

In those genotypes that responded well, significant improvement in embryo length and morphology were seen using 5 or 10 mg/L $GA_3$ or 5 mg/L $GA_{4/7}$ compared to the control samples without any added growth hormones. Average length without hormones was 2.1 mm compared with 2.3-2.4 mm when 5 and 10 mg/L $GA_3$ or $GA_{4/7}$ was used. Embryos developed using the $GA_3$/ABA combinations averaged a bit over 1.9 mm in length. Visual evaluation of the $GA_{4/7}$ embryos showed them to be slightly more tapered in the hypocotyl and root cap regions than those grown on the $GA_3$ media. While the trials using the combination of 5 mg/L GA with ABA showed a decrease in embryo length, there was a significant change in visual morphology. The suspensor/rootcap region was more similar to that seen in zygotic embryos in seeds. The suspensor elongated and remained narrow and the embryo tapered to flow smoothly into the suspensor, as seen in FIG. 6B. Without hormones, or with either $GA_3$ or ABA alone, the suspensor cells proliferate and the embryo appears to emerge from a stumpy mass of cells, as shown in FIG. 6A.

What appears here to be a morphological synergism between GA and ABA is interesting because these hormones are reported to be antagonists in most of the literature relating to angiosperms.

EXAMPLE 4

This factorial experiment employed five levels of $GA_{4/7}$, 0, 1, 2.5, 5, and 7.5 mg/L, each with 0 or 10 mg/L ABA. Singulation and rinsing were as described in Example 2. The basal development medium was modified slightly, however. Sucrose was reduced to 40,000 mg/L (4%) and lactose was raised to 33.0 g/L (3.30%). Five genotypes of Douglas-fir were tested. Three had been used in either the trials of Examples 2 or 3 and two were new to this trial. One of the new genotypes performed poorly. The others produced good cotyledonary embryos.

The following conclusions can be drawn from this test. $GA_{4/7}$ alone in all concentrations increased embryo elongation relative to the control samples lacking GA. All combinations of GA and ABA also showed increased length. ABA alone at 10 mg/L produced embryos of comparable length to the control sample. These lengths were measured as follows:

TABLE 3

| ABA | $GA_{4/7}$ | Embryo length, mm |
|---|---|---|
| 0 | 0 | 1.95 |
| 0 | 1 | 2.2 |
| 0 | 2.5 | 2.3 |
| 0 | 5 | 2.35 |
| 0 | 7.5 | 2.45 |
| 10 | 0 | 2.0 |
| 10 | 1 | 2.4 |
| 10 | 2.5 | 2.45 |
| 10 | 5 | 2.4 |
| 10 | 7.5 | 2.35 |

The differences in length between the control and 10 mg/L ABA samples are not statistically different nor are the differences between any of the GA treated samples. However, differences between the samples with and without GA treatment are highly significant.

Visual observation showed embryo shape to be improved in treatments combining GA and ABA with the best treatment qualitatively being 10 mg/L ABA and 7.5 mg/L $GA_{4/7}$. Since these were the highest levels used of both hormones the suggestion is present to explore the effect of still increased levels.

EXAMPLE 5

To follow up the possibility of even better performance at higher levels of hormones another factorial experiment was conducted using 0, 10, and 20 mg/L ABA and 0, 5, 7.5, and 10 mg/L $GA_{4/7}$. Other than the hormone levels, media composition and earlier treatments were the same as those of Example 4. Four genotypes were used. Three of these were common with those of the previous trials. The one genotype that did not produce embryos in Example 2 yielded good embryos in this trial.

Results were similar to those of the previous Example. All treatments using $GA_{4/7}$ in any concentration produced longer embryos than control cultures lacking this hormone. ABA did not appear to have any effect on embryo length although with no GA present embryo length trended downward with increasing ABA concentration. Embryos grown on any of the $GA_{4/7}$ media averaged about 2.4 mm while those without were about 1.9-2.0 mm in length. $GA_{4/7}$ alone improved embryo shape. Combinations of ABA and $GA_{4/7}$ produced the best embryos. These embryos are similar to those sketched in FIG. 6B. In particular, embryos with the combined treatment showed longer cotyledons and greater taper and were most similar to zygotic embryos. All of the embryos were classified as to one of five shapes. A nonparametric statistical test showed the shape differences noted above to be significant. There did not appear to be any advantage to hormone levels higher than those of Example 4. Again, the best appearing embryos were those developed on medium containing 10 mg/L ABA and 7.5 mg/L $GA_{4/7}$.

A representative sample of the embryos were sectioned for organ measurement. The "Control" sample had no hormones present in the development medium. "GA Alone" used 7.5 mg/L of $GA_{4/7}$ in the development medium. "GA+ABA" had 7.5 mg/L $GA_{4/7}$ and 10 mg/L ABA in the development medium. Results appear in the following table.

TABLE 4

| Treatment | Cotyledon Length, mm | Hypocotyl Length, mm | Root Cap Length, mm | Hypocotyl Width, mm | Total Length, mm |
|---|---|---|---|---|---|
| Zygotic | 0.89 | 1.51 | 1.17 | 0.49 | 3.57 |
| Control | 0.18 | 0.55 | 0.49 | 0.51 | 1.22 |
| GA Alone | 0.39 | 0.69 | 0.55 | 0.49 | 1.63 |
| GA + ABA | 0.33 | 0.60 | 0.60 | 0.44 | 1.52 |

Observation and measurement of the apical dome can provide an indicator of expected successful germination. These measurements were also made on the above sections and are reported in the following table.

TABLE 5

| Treatment | Mean Dome Height, mm | Maximum Dome Height, mm | Minimum Dome Height, mm | Embryos With Dome, % |
|---|---|---|---|---|
| Zygotic | 0.112 | 0.184 | 0.0490 | 100 |
| Control | 0.033 | 0.061 | 0 | 82.2 |
| GA Alone | 0.039 | 0.084 | 0 | 97.2 |
| GA + ABA | 0.037 | 0.069 | 0.015 | 100 |

While not yet equal in size to zygotic embryos, the improvements in quality brought about by incorporation of GA or GA and ABA in the development media are clearly evident from the above tables.

It would appear that each hormone plays an important role in embryo development. GA seems to increase embryo length and improve cotyledon and apical dome development. ABA may be critical to development in the root cap/suspensor region in addition to its role in prevention of premature germination and accumulation of storage products.

Selected embryos from two genotypes were placed on a germination medium as described in Table 2. Embryos showing a root at least 3 mm long and an epicotyl were considered germinated. There was statistically significant increase in germination of embryos grown on media containing only $GA_{4/7}$ at all levels as was also the case for those grown on ABA/GA containing media. ABA alone in either concentration did not increase germination percentage.

It would appear to be beneficial to somatic embryo development to begin addition of gibberellins even earlier in the culturing process than has been heretofore described. In the case of Douglas-fir, this benefit may accrue by addition of GAs to at least the final and probably the earlier singulation stages. There are further indications that GAs may have beneficial effects for all coniferous species when added to the late stage proembryo development medium or even to the maintenance medium for the early stage proembryo cultures. On the other hand, it appears that the benefit of GAs is not fully realized, or not realized at all, when added later than about the midpoint of the cotyledonary embryo development period. This will be illustrated by the following examples.

EXAMPLE 6

Douglas-fir embryos from two genotypes were cultured as in the previous examples but with the following modifications in the third singulation shake. In one set of cultures the normal 5 mg/L ABA was supplemented with 0, 1, 2.5, and 5 mg/L $GA_{4/7}$. In the other set the ABA was replaced with 1, 2.5, and 5 mg/L $GA_{4/7}$. After the one week shake period the cells were rinsed as in the earlier examples and plated on one cotyledonary embryo development medium which lacked growth hormones entirely, and on another which contained 10 mg/L ABA and 7.5 mg/L $GA_{4/7}$. Otherwise the development media were similar in composition to that of Examples 4 and 5.

At the end of the development period, embryos of both genotypes grown using the modified hormone regimen in the third singulation shake were not significantly different in size or appearance from the control embryos using 5 mg/L ABA alone in the third singulation shake culture. The embryos were placed on germination medium and left for three weeks in the dark. At that time it became apparent that there were differences in germination. Statistically significant increases in root length occurred with embryos cultured with 2.5 or 5 mg/L $GA_{4/7}$ plus 5 mg/L ABA in the third shake and then further developed on a the medium containing 10 mg/L ABA and 7.5 mg/L $GA_{4/7}$. Thus, while not initially visually apparent, there appears to be ultimate benefit in extending GA treatment back into the singulation stage.

EXAMPLE 7

Since it was shown to be advantageous in Douglas-fir culture to add GA to the media of the singulation stage used prior to the cotyledonary embryo development medium, an additional set of trials was run to investigate the effect of GA used even earlier in the process. In the present example $GA_{4/7}$ was added to the Stage II maintenance medium (refer to Table 2) for Douglas-fir early proembryos. GA levels were 0, 0.1, 0.5, and 1.0 mg/L. These were combined with ABA at 0 and 0.5 mg/L in a factorial experiment design. Subcultures to fresh media were made on a weekly basis for eight weeks. It is noted that neither ABA or GA is ordinarily used in the maintenance media. Three genotypes were used in the trial.

Embryos were rated visually every week for each genotype and the ratings were averaged over the trial. A rating of 0 indicates that no embryos are visible among the cell mass. A rating of 1 indicates that embryonic heads are clearly visible. A 2 rating is given when the heads and attached suspensors have achieved at least a late stage proembryo form. A rating of 3 indicates further enlargement of the head and attached suspensors to a size typical of the embryos at the end of the singulation process. Results are given in the following table.

TABLE 6

| Trial No. | ABA, mg/L | GA, mg/L | Proembryo Rating | | |
|---|---|---|---|---|---|
| | | | Geno. 711 | Geno. 917.28 | Geno. 925.22 |
| 1 | 0 | 0 | 1.9 | 1.6 | 1.4 |
| 2 | 0 | 0.1 | 2.1 | 1.7 | 1.5 |
| 3 | 0 | 0.5 | 2.2 | 1.9 | 1.6 |
| 4 | 0 | 1.0 | 2.2 | 1.8 | 1.6 |
| 5 | 0.5 | 0 | 2.3 | 1.9 | 1.7 |
| 6 | 0.5 | 0.1 | 2.4 | 1.8 | 1.7 |
| 7 | 0.5 | 0.5 | 2.4 | 1.8 | 1.8 |
| 8 | 0.5 | 1.0 | 2.5 | 1.8 | 1.8 |

Results clearly show that either GA alone or ABA alone improve embryo quality. The combination of GA and ABA appears to have additive effect, at least in two of the genotypes. It has been generally established that larger proembryos entering the development stage will most usually result in larger and more robust cotyledonary embryos.

NORWAY SPRUCE CULTURE

While the media compositions and growth hormone usages described in the previous examples of this application are those that we presently regard as optimum for Douglas-fir, different concentrations and mixtures appear more suitable for other species. The following tables show preferred media for culture of Norway spruce by somatic embryogenesis.

TABLE 7

| | Picea Abies Basic Culture Media | |
|---|---|---|
| | Concentration, mg/L | |
| Constituent | A[(1)] | B[(2)] |
| BASAL SALTS | | |
| $NH_4NO_3$ | — | 206.3 |
| KCl | 372.5 | — |
| $KNO_3$ | 50.0 | 2340.0 |
| $KH_2PO_4$ | 85.0 | 85.0 |
| $MgSO_4.7H_2O$ | 160.0 | 185.0 |
| $CaCl_2.6H_2O$ | 220.0 | 220.0 |
| KI | 0.415 | 0.415 |
| $H_3BO_3$ | 3.10 | 3.10 |
| $MnSO_4.H_2O$ | 8.45 | 8.45 |
| $ZnSO_4.7H_2O$ | 4.30 | 4.30 |
| $NaMoO_4.2H_2O$ | 0.125 | 0.125 |
| $CuSO_4.5H_2O$ | 0.0125 | 0.0125 |
| $CoCl_2.6H_2O$ | 0.0125 | 0.0125 |
| $FeSO_4.7H_2O$ | 13.90 | 13.93 |
| $Na_2$ EDTA | 18.65 | 18.63 |
| ORGANIC ADDITIVES | | |

TABLE 7-continued

Picea Abies Basic Culture Media

| Constituent | Concentration, mg/L | |
|---|---|---|
| | A[1] | B[2] |
| Sucrose | 10,000. | 30,000. |
| myo-Inositol | 50.0 | 1000.0 |
| Casamino acids | — | 500.0 |
| L-Glutamine | 750.0 | 450.0 |
| Thiamine.HCl | 0.05 | 1.00 |
| Pyridoxine.HCl | 0.05 | 0.50 |
| Nicotinic acid | 0.25 | 0.50 |
| Glycine | — | 2.00 |
| L-Asparagine | 50.0 | — |
| pH | 5.8 | 5.7 |

[1]Institute of Paper Chemistry medium (Verhagen and Wann 1989)
[2]Gupta and Durzan medium BM$_3$ (1986b).

TABLE 8

Composition of Picea Abies Media for Different Stage Treatments

BM$_I$ - Induction Medium
BM$_A$[1] + NAA[3] (10.8 μM) + BAP[4] (4.4 μM) + 7.0 g/L Difco agar.
BM$_M$ - Maintenance and Multiplication Medium
BM$_B$[2] + 2,4-D[5] (5 μM) + BAP (2 μM) + KIN[6] (2 μM).
6.0 g/L Difco agar added if solid medium is desired.
BM$_D$ - Cotyledonary Embryo Development Medium
BM$_B$ + 40.0 mg/L Argine + 100 mg/L Asparagine + 6.0 g/L Tissue Culture Agar + Abscisic acid (as spedified) + Activated charcoal 1.25 g/L. KNO$_3$ is reduced to 1170 mg/L in basal salts.
BM$_G$ - Germination Medium
BM$_B$ with KNO$_3$ reduced to 1170 mg/L, myo-Inositol reduced to 100 mg/L, Sucrose reduced to 20.0 g/L, and L-Glutamine and Casamino acids removed. 2.5 g/L of Adsorbent and 6.0 g/L of Tissue Culture Agar are added.

[1]Basal medium A from Table 4
[2]Basic medium B from Table 4
[3]2-Naphthylacetic acid (Naphthalene-2-acetic acid)
[4]N$^6$-Benzylaminopurine
[5]2,4-Dichlorophenoxyacetic acid
[6]Kinetin

EXAMPLE 8

Norway spruce late stage proembryos were plated directly from a maintenance medium onto solid development media containing 50 mg/L ABA and concentrations of GA$_{4/7}$ of 0, 1, 2.5, 5, 7.5, 10, and 15 mg/L. After 6 weeks development it was noted that embryo yield was significantly reduced in all cultures where GA$_{4/7}$ was present. Little difference in yield was seen at any concentration of GA$_{4/7}$. The magnitude of the differences was from an average of about 57 embryos per plate when no GA was present to about 33 embryos per plate for the GA containing cultures. However, as early as three weeks after plating on the development media, visible differences were seen between embryos on the GA treated media and those in the control culture lacking GA. Ultimately the cotyledonary embryos from the GA containing cultures showed increased length and greater taper and generally had greater resemblance to zygotic embryos. Concentrations of 5 and 10 mg/L GA$_{4/7}$ were most effective.

EXAMPLE 9

This trial was made with some development media having activated charcoal removed in order to better understand the specific individual and combined effects of ABA and GA. In those media lacking charcoal, hormones were reduced by a factor of 10 and transfers to fresh media were made on a biweekly basis. At the time of the first transfer, inorganic nitrogen (KNO$_3$) was halved and amino acid concentration increased (see Table 9 footnotes). ABA and GA$_{4/7}$ concentration was held constant during the entire development time for any given treatment.

Development media were modified as shown in the following table.

TABLE 9

| Media No. | Initial Medium | First Transfer | Second Transfer | ABA mg/L | GA 4/7 mg/L | Activated Charcoal, % |
|---|---|---|---|---|---|---|
| 1 | a | No transfers made | | 50 | 0 | 0.125 |
| 2 | a | No transfers made | | 50 | 15 | 0.125 |
| 3 | b | c | c | 0 | 0.1 | 0 |
| 4 | b | c | c | 0 | 0.5 | 0 |
| 5 | b | c | c | 0 | 1.5 | 0 |
| 6 | b | c | c | 5 | 0 | 0 |
| 7 | b | c | c | 5 | 0.5 | 0 |
| 8 | b | c | c | 5 | 1.0 | 0 |
| 9 | b | c | c | 5 | 1.5 | 0 |
| 10 | b | c | c | 0 | 0 | 0 |

Basal Medium Inorganic Nitrogen/Amino Acid Nitrogen
a. 2340 mg/L KNO$_3$, 40 mg/L arginine, 100 mg/L asparagine,
b. 2340 mg/L KNO$_3$, 0 mg/L arginine, 0 mg/L asparagine.
c. 1170 mg/L KNO$_3$, 40 mg/L arginine, 100 mg/L asparagine.

Average embryo lengths were measured as follows:

TABLE 10

| Treatment No. | Embryo Yield, Number per Plate | Embryo Length, mm |
|---|---|---|
| 1 | 25 | 2.77 |
| 2 | 28.5 | 3.05 |
| 3 | 2 | — |
| 4 | 2 | — |
| 5 | 2 | — |
| 6 | 12 | 2.93 |
| 7 | 12 | 3.12 |
| 8 | 13 | 3.13 |
| 9 | 14 | 2.92 |
| 10 | 2 | — |

Treatments 3, 4, 5, and 10, lacking both ABA and activated charcoal, developed only a few poor quality precociously germinating embryos. Thus, either no hormones, or GA alone, were insufficient to generate useful quantities of good quality embryos. Yields improved, as did embryo size and shape, when GA and ABA were used together, even when charcoal was absent (Treatments 7-9). Shape of these embryos was improved over Treatment 6 which had ABA but lacked GA. Yields of normal cotyledonary embryos were significantly higher in the two treatments (1 and 2) containing activated charcoal. Treatment 2, containing activated charcoal, GA, and ABA produced the largest embryos. These also had a significantly improved shape; i.e., more closely resembled zygotic embryos in morphology.

As with Douglas-fir, gibberellins appear to have a role in determining embryo size and interact with ABA in determining shape and yield. This is contrary to the findings of others that GA and ABA are antagonistic.

Following embryo development the somatic embryos may be retained for some period of time in cold storage. They may be converted into artificial seeds for field or nursery planting. Alternatively, they may be placed immediately on a germination medium for conversion into plantlets prior to planting in soil.

It should be recognized that there is not one single set of culturing conditions that will be suitable for achieving somatic embryogenesis of all species or for all genotypes within a species. Tissue culture as a whole is a highly unpredictable science. This statement has even greater applicability to somatic embryogenesis. Adjustments in the mineral and plant hormone constituents of the culture media must frequently be made depending on the particular species and genotype being cultured. This applies to each of the various stages of culturing from explants to plantlets. These adjustments are considered to be within the routine experimental capability of those skilled in the art of tissue culture. The important discovery of the present invention is the usefulness of various gibberellins for improvement of embryo quality. Gibberellins have been found beneficial by including them in the process as early as the proembryo maintenance cultures. They are particularly useful when combined with abscisic acid in the cotyledonary embryo development media. These procedures have given results that are far superior in terms of success and consistency than any process reported heretofore. The process has been successfully applied to several species and many genotypes of coniferous plants studied to date and appears to be of general use for all coniferous species.

It will be understood that many variations can be made in the procedures described for the various culturing stages while still remaining within the spirit of the present invention. It is the intention of the inventors that such variations should be included within the scope of their invention if found defined within the following claims.

BIBLIOGRAPHY

Abo El-Nil, Mostafa M.
  1980—Embryogenesis of gymnosperm forest trees. U.S. Pat. No. 4,217,730.
Ammirato, Philip V.
  1977—Hormonal control of somatic embryo development from cultured cells of caraway: interactions of abscisic acid, zeatin, and gibberellic acid. *Plant Physiology* 59:579-586.
  1983—The regulation of somatic embryo development in plant cell cultures: suspension culture techniques and hormone requirements. *Bio/Technology* 1(3): 68-74.
Chalupa, V.
  1990a—Somatic embryogenesis and plant regeneration in *Quercus petraea* (Matt.) Liebl., *Tilia platyphyllos* Scop. and *Aesculus hippocastanum* L. *Lesnictvi* (Prague) 36:599-604.
  1990b—Plant regeneration by somatic embryogenesis from cultured immature embryos of oak (*Quercus robur* L.) and linden (*Tilia cordata* Mill. *Plant Cell Reports* 9:398-401.
Cruz, Gil S., Jorge M. Canhoto, and Maria Alexandra V. Abreu
  1990—Somatic embryogenesis and plant regeneration from zygotic embryos of *Feijoa sellowiana* Berg. *Plant Science* 66:263-270.
Durzan, D. J. and P. K. Gupta
  1987—Somatic embryogenesis and polyembryogenesis in Douglas-fir cell suspension cultures. *Plant Science* 52:229-235.
Eapen, S., V. Abraham, M. Gerdemann, and O. Schieder
  1989—Direct somatic embryogenesis, plant regeneration and evaluation of plants obtained from mesophyll protoplasts of *Brassica juncea*. *Annals of Botany* 63:369-372.
Eapen, Susan, and Leela George
  1990—Ontogeny of somatic embryos of *Vigna aconitifolia, Vigna mungo* and *Vigna radiata*. *Annals of Botany* 66:219-226.
Evans, M. L.
  1984—Functions of hormones at the cellular level of organization. In *Hormonal Regulation of Development II*, Tom K. Scott Ed., pp 23-79, Springer-Verlag, New York.
Ferriera, Alfredo Gui, Ching Yeh-Hu, and Eliane Romanato Santarem
  1990—Somatic embryogenesis of soybean *Glycine max* (1.) Merrill, Brazilian cultivars Ivorá and IAS-5. *Phyton* (Buenos Aires) 51 (2): 139-144.
Garcia-Maya, M., J. M. Chapman, and M. Black
  1990—Regulation of α-amylase formation and gene expression in the developing wheat embryo: role of abscisic acid, the osmotic environment and gibberelin. *Planta* 181:296-303.
Ghosh, Biswajit and Sumitra Sen
  1991—Plant regeneration through somatic embryogenesis from spear callus culture of *Asparagus cooperi* Baker. *Plant Cell Reports* 9:667-670.
Gmitter, F. G. Jr., X. B. Ling, and X. X. Deng
  1990—Induction of triploid citrus plants from endosperm calli in vitro. *Theoretical and Applied Genetics* 80:785-790.
Gupta, Pramod K. and Don J. Durjan
  1986—Plantlet regeneration via somatic embryogenesis from subcultured callus of mature embryos of *Picea abies* (Norway spruce). *In Vitro Cellular & Developmental Biology* 22:685-688.
Gupta, Pramod K. and Gerald S. Pullman
  1990—Method for reproducing coniferous plants by somatic embryogenesis. U.S. Pat. No. 4,957,866.
  1991—Method for reproducing coniferous plants by somatic embryogenesis using abscisic acid and osmotic potential variation. U.S. Pat. No. 5,036,007.
Hakman, Inger and Sara von Arnold
  1985—Plantlet regeneration through somatic embryogenesis in *Picea abies*. *Journal of Plant Physiology* 121:149-158.
Kochba, J., P. Spiegel-Roy, H. Neumann, and S. Saad.
  1978—Stimulation of embryogenesis in citrus ovular callus by abscisic acid, ethepon, 2-chloroethyltrimethyl ammonium chloride, and Alar and its suppression by gibberellic acid. *Z. Pflanzenphysiol. Bd.* 89:427-432.
Lakshmi Sita, G.
  1985—Sandalwood (*Santalum album*). In *Biotechnology in Agriculture and Forestry* 1: *Trees I*, Y. P. S. Bajaj, ed. Springer-Verlag, New York.
Manrique, S. L. and W. Roca
  1987—Effect of the photoperiod and the culture medium on somatic embryogenesis and a histological analysis of the process in the cassava *Manihot esculenta* Crantz. *Acta Agronomica* (Palmira) 37 (2): 7-18.
Murashihe, Toshio and Folke Skoog
  1962—A revised medium for rapid growth and bio assays with tobacco tissue cultures. *Physiologia Plantarum* 15:473-493.
Nolan, Randall C. and Tuan-Hua David Ho
  1988—Hormonal regulation of α-amylase expression in barley aleurone layers: the effects of gibberellic acid removal and abscisic acid and phaseic acid treatments. *Plant Physiology* 88:588-593.
Noriega, Clemencia and Maro R. Söndahl 1991—Somatic embryogenesis in hybrid tea roses. *Bio/Technology* 9:991–993.

Pullman. Gerald S. and Pramod K. Gupta
  1991—Method for reproducing coniferous plants by somatic embryogenesis using adsorbent materials in the development stage media. U.S. Pat. No. 5,034,326.

Rajasekaran, K., M. B. Hein, and I. K. Vasil
  1987—Endogenous abscisic acid and IAA and somatic embryogenesis in cultured leaf explants of *Pennisetum purpureum* Schum.: effects in vivo and in vitro of glyphosphate fluridone, and paclobutrazol. *Plant Physiology* (Bethesda) 84:47–51.

Rangaswamy, N. S.
  1986—Somatic embryogenesis in angiosperm cell tissue and organ cultures. *Proceedings Indian Academy of Sciences (Plant Sciences)* 96 (4): 247–271.

Sondahl, Maro R., T. B. Sereduk, Claudia M. Bellato, and Zhenghua Chen
  1988—Somatic embryogenesis and plant regeneration of cacao. European Patent Application A 0 293 598.

Sponsel, Valerie M.
  1987—Gibberellin biosynthesis and metabolism. In *Plant Hormones and their Role in Plant Growth and Development*, Peter J. Davies, Ed., pp 43–69, Martinus Nijhoff, Boston.

Tisserat, Brent and Toshio Murashige
  1977—Probable identity of substances in citrus that repress asexual embryogenesis. *In Vitro* 13:785–789.

Trolinder, Norma L., and J. R. Goodin
  1988—Somatic embryogenesis in cotton (Gossypium). II: requirements for embryo development and plant regeneration. *Plant Cell, Tissue and Organ Culture* 12:43–53.

Verhagen, Shirley A. and Steven R. Wann
  1989—Norway spruce somatic embryogenesis: high-frequency initiation from light cultured mature embryos. *Plant Cell, Tissue and Organ Culture* 16:103–111.

We claim:

1. A method of reproducing coniferous plants by somatic embryogenesis which comprises:
  placing an explant on an initiation culture medium and growing a culture containing early stage proembryos;
  transferring the proembryos to a cotyledonary embryo development medium containing plant growth hormones comprising at least one active gibberellin in an amount of 0.5–50 mg/L of medium and abscisic acid in an amount of about 1–50 mg/L and growing cotyledonary embryos.

2. The method of claim 1 in which the development medium further includes an adsorbent material to gradually reduce the level of the plant growth hormones over time.

3. The method of claim 1 in which the adsorbent material is activated charcoal.

4. The method of claim 1 in which the gibberellins are selected from the group consisting of $GA_3$, $GA_4$, $GA_7$, and mixtures thereof.

5. The method of claims claim 1 which further includes multiplying the proembryos by transfer from the initiation medium to a maintenance medium prior to transfer to the late stage development medium.

6. The method of claim 5 in which the maintenance medium also includes abscisic acid in an amount of about 0.05–15 mg/L.

7. The method of claim 6 in which the maintenance medium also includes an active gibberellin in an amount of about 0.05–15 mg/L.

8. The method of claim 5 in which the maintenance medium includes abscisic acid in an amount of about 0.05–15 mg/L. and an active gibberellin in an amount of about 0.05–15 mg/L.

9. The method of claim 1 in which the coniferous species is Douglas-fir and which further includes at least one intermediate liquid shake culture between the initiation culture and cotyledonary embryo development culture in order to singulate any clumped proembryos, the medium of said liquid singulation culture containing exogenous abscisic acid in an amount of about 5–15 mg/L.

10. The method of claim 9 in which the liquid singulation culture also contains an active gibberellin in an amount of about 0.05–15 mg/L.

11. The method of claim 10 in which the osmotic potential of the cotyledonary embryo development medium is at least about 350 mM/kg.

12. A method of reproducing coniferous plants by somatic embryogenesis which comprises:
  placing an explant on an initiation culture medium and growing a culture containing early stage proembryos;
  transferring the proembryos from the initiation medium to a maintenance medium containing plant growth hormones comprising at least one active gibberellin in an amount of about 0.05–15 mg/L of medium and abscisic acid in an amount of about 0.05–15 mg/L in order to multiply the embryos for further development into cotyledonary embryos.

13. The method of claim 12 which further includes transferring the proembryos from the maintenance medium to a cotyledonary embryo development medium for further development into cotyledonary embryos.

14. The method of claim 13 in which the development medium includes plant growth hormones selected from the group consisting of abscisic acid, active gibberellins and mixtures thereof.

15. The method of claim 14 in which the development medium includes abscisic acid in an amount of about 1–50 mg/L.

16. The method of claim 14 in which the development medium includes an active gibberellin in an amount of about 0.5–50 mg/L.

17. The method of claim 14 in which the development medium includes both an active gibberellin in an amount of about 0.5–50 mg/L and abscisic acid in an amount of about 0.5–50 mg/L.

18. The method of claims 14, 15, or 16 in which the development medium further includes an adsorbent material to gradually reduce the level of the plant growth hormones over time.

19. The method of claim 18 in which the adsorbent material is activated charcoal.

20. The method of claims 12, 14, 16, or 17 in which the active gibberellin is selected from the group consisting of $GA_3$, $GA_4$, $GA_7$, and mixtures thereof.

* * * * *